United States Patent
Ito (10) Patent No.: US 9,018,556 B2
(45) Date of Patent: Apr. 28, 2015

(54) MICROPARTICLE SORTING METHOD

(71) Applicant: Sony Corporation, Tokyo (JP)

(72) Inventor: Tatsumi Ito, Kanagawa (JP)

(73) Assignee: Sony Corporation (JP)

( * ) Notice: Subject to any disclaimer, the term of this patent is extended or adjusted under 35 U.S.C. 154(b) by 0 days.

(21) Appl. No.: 13/943,956

(22) Filed: Jul. 17, 2013

(65) Prior Publication Data

US 2014/0027356 A1    Jan. 30, 2014

(30) Foreign Application Priority Data

Jul. 24, 2012   (JP) ................. 2012-164038

(51) Int. Cl.
*B01L 3/00*   (2006.01)
*B07C 5/34*   (2006.01)
*G01N 15/14*   (2006.01)

(52) U.S. Cl.
CPC ......... *B07C 5/3416* (2013.01); *B01L 3/502761* (2013.01); *B01L 2200/0652* (2013.01); *B01L 2300/0816* (2013.01); *B01L 2300/0864* (2013.01); *B01L 2400/0481* (2013.01); *B01L 2400/049* (2013.01); *G01N 2015/149* (2013.01); *G01N 15/1484* (2013.01); *Y10S 209/932* (2013.01)

(58) Field of Classification Search
CPC ................. B07C 5/342; B07C 5/3425; B01L 2300/0819; B01L 2300/0861; B01L 2300/0864; B01L 2300/0877; B01L 2300/14
USPC ......... 209/552, 576, 577, 586–588, 643, 932; 422/502–504
See application file for complete search history.

(56) References Cited

U.S. PATENT DOCUMENTS

| | | | |
|---|---|---|---|
| 4,936,465 A * | 6/1990 | Zold | 209/3.1 |
| 7,258,774 B2 * | 8/2007 | Chou et al. | 204/450 |
| 8,216,852 B2 * | 7/2012 | Chow et al. | 436/174 |
| 8,567,608 B2 * | 10/2013 | Deshpande et al. | 209/552 |
| 8,623,294 B2 * | 1/2014 | Asogawa et al. | 422/502 |
| 2012/0078531 A1 * | 3/2012 | Lo et al. | 702/21 |

FOREIGN PATENT DOCUMENTS

| | | |
|---|---|---|
| JP | 2005-538727 | 12/2005 |
| JP | 2009-100698 | 5/2009 |

* cited by examiner

*Primary Examiner* — Joseph C Rodriguez
(74) *Attorney, Agent, or Firm* — Sheridan Ross P.C.

(57) ABSTRACT

There is provided a microparticle sorting method, including a procedure of collecting a microparticle in a fluid that flows through a main channel in an area that is formed in a manner that a vertical cross-section increases in a flow direction of the fluid at a branch channel which is in communication with the main channel by generating a negative pressure in the branch channel.

14 Claims, 10 Drawing Sheets

1a: MICROCHIP
12: SAMPLE FLUID CHANNEL
14: SHEATH FLUID CHANNEL
16: SORTING CHANNEL
31: ACTUATOR
161: PRESSURE CHAMBER
311: DISPLACEMENT PLATE
11: SAMPLE FLUID INLET
13: SHEATH FLUID INLET
15: MAIN CHANNEL
17: WASTE CHANNEL
156: COMMUNICATION OPENING
162: COLLECTION OPENING

S: SAMPLE FLUID LAMINAR FLOW
15: MAIN CHANNEL
17: WASTE CHANNEL
T: SHEATH FLUID LAMINAR FLOW
16: SORTING CHANNEL
156: COMMUNICATION OPENING

PULSE WAVEFORM

B

STEP WAVEFORM

C

UNDERSHOOT-STEP WAVEFORM

FIG. 10

MICROPARTICLE SORTING METHOD

BACKGROUND

The present technology relates to a microparticle sorting method. More specifically, the present technology relates to a microparticle sorting method that separates and recovers only target microparticles from the microparticles that are flowing along a channel.

A microparticle sorting apparatus that forms a microparticle-containing sheath flow in a channel, detects fluorescence and scattered light emitted from the microparticles by irradiating light on the microparticles in the sheath flow, and separates and recovers a microparticle group (population) that exhibits a predetermined optical characteristic is known. For example, in a flow cytometer, a specific type of cell only is separated and recovered by labeling a plurality of types of cell included in a sample with a fluorescent dye and optically identifying the fluorescent dye labeled on each cell.

In JP 2009-100698A and JP 2005-538727T, microchip-type microparticle sorting apparatuses are disclosed that perform analysis by forming a sheath flow in a channel formed on a microchip that is made from plastic, glass or the like.

The microparticle sorting apparatus disclosed in JP 2009-100698A controls the feeding direction of the sheath flow at a branching portion between an introduction channel in which the sheath flow is formed and a branch channel in communication with the introduction channel by generating an air bubble based on laser irradiation at the branching portion. According to this microparticle sorting apparatus, controlling the feeding direction of the sheath flow at the branching portion with an air bubble enables just the target microparticles to be collected into the branch channel from the introduction channel and sorted.

Further, the microfluidic system disclosed in JP 2005-538727T sorts target microparticles by using an actuator to control the feeding direction of a sheath flow at a channel branching portion. In this microfluidic system, the actuator changes the feeding direction of the sheath flow by pressing against a chamber that is connected to a branching portion between an introduction channel in which the sheath flow is formed and a branch channel in communication with the introduction channel to push out fluid in the chamber.

SUMMARY

For microchip-type microparticle sorting apparatuses, in order to further increase the speed and accuracy of analysis, there is a demand for a technology for rapidly and stably extracting only target microparticles from a sheath flow that is flowing through a channel.

According to an embodiment of the present technology, there is provided a microparticle sorting technology that can rapidly and stably extract only target microparticles from a sheath flow that is flowing through a channel.

According to an embodiment of the present technology, there is provided a microparticle sorting method, including a procedure of collecting a microparticle in a fluid that flows through a main channel in an area that is formed in a manner that a vertical cross-section increases in a flow direction of the fluid at a branch channel which is in communication with the main channel by generating a negative pressure in the branch channel.

In this microparticle sorting method, by forming a vertical cross-section to increase in size in the flow direction of a fluid along a branch channel so that the microparticles are collected in an area whose inner space has expanded, the microparticles that have been collected in the branch channel can be held and accumulated without flowing back out into the main channel.

According to the microparticle sorting method of the present technology, in the procedure, the negative pressure may be generated by an actuator applying a force that deforms an inner space of the branch channel to cause a volume of the inner space to increase.

According to the microparticle sorting method of the embodiment of the present technology, in the procedure, an amount of increase in the volume by the actuator may be greater than a volume of the branch channel from a communication opening to the area, the communication opening leading to the main channel.

According to the microparticle sorting method of the embodiment of the present technology, in the procedure, the fluid including the microparticle may flow into the area as a jet.

According to the microparticle sorting method of the embodiment of the present technology, in the procedure, a pressure change having a pulse waveform, a step waveform, or an undershoot-step waveform may be produced in the branch channel.

According to the microparticle sorting method of the embodiment of the present technology, in the procedure, the negative pressure may be generated by the actuator applying a force that deforms an inner space of the area to cause a total volume of the inner space of the branch channel to increase.

According to the microparticle sorting method of the embodiment of the present technology, the main channel and the branch channel may be formed inside a microchip, and the actuator is arranged in contact with a position corresponding to the area on a surface of the microchip.

In an embodiment of the present technology, the term "microparticle" has a broad meaning that includes biologically-relevant microparticles such as cells, microbes, ribosomes and the like, as well as synthetic particles such as latex particles, gel particles, industrial particles and the like.

Examples of biologically-relevant microparticles include the chromosomes, liposomes, mitochondria, organelles (cell organelles) that form various cells. Examples of cells include animal cells (hematopoietic cells etc.) and plant cells. Examples of microbes include bacteria such as $E.\ coli$, viruses such as tobacco mosaic virus, fungi such as yeast and the like. Further example of biologically-relevant microparticles includes nucleic acids, proteins, complexes of these and the like. Examples of industrial particles include organic or inorganic polymer materials, metals and the like. Examples of organic polymer materials include polystyrene, styrene-divinyl benzene, poly methyl methacrylate and the like. Examples of inorganic polymer materials include glass, silica, magnetic materials and the like. Examples of metals include metal colloids, aluminum and the like. Although the shape of these microparticles is usually spherical, the microparticles may also have a non-spherical shape. Further, the size and mass of these microparticles is not especially limited.

According to the embodiments of the present technology described above, a microparticle sorting technology is provided that can rapidly and stably extract only target microparticles from a sheath flow that is flowing through a channel.

BRIEF DESCRIPTION OF THE DRAWINGS

FIG. 3 is a diagram illustrating a configuration of the microchip 1a;

FIG. 4 is a diagram illustrating a configuration of the microchip 1a;

FIG. 5 is a diagram illustrating a configuration of a branching portion between a main channel 15 and a sorting channel 16 of the microchip 1a;

FIG. 7 is a diagram illustrating functions of a pressure chamber 161 in the microchip 1a;

FIG. 8 is a diagram illustrating a configuration of a modified example of the microchip 1a;

DETAILED DESCRIPTION OF THE EMBODIMENT(S)

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted. The description will be made in the following order.

1. Microparticle sorting apparatus and microchip for microparticle sorting that are capable of implementing the microparticle sorting method according to an embodiment of the present technology
(Overall configuration of the apparatus)
(Microchip configuration)
2. Microparticle sorting method according to an embodiment of the present technology
(Sorting operation)
(Drive signal)
3. Modified example of the microparticle sorting method according to an embodiment of the present technology
4. Microparticle sorting program 1. Microparticle Sorting Apparatus and Microchip for Microparticle Sorting that are capable of Implementing the Microparticle Sorting Method According to an Embodiment of the Present Technology (Overall Configuration of the Apparatus)

Figure 1:
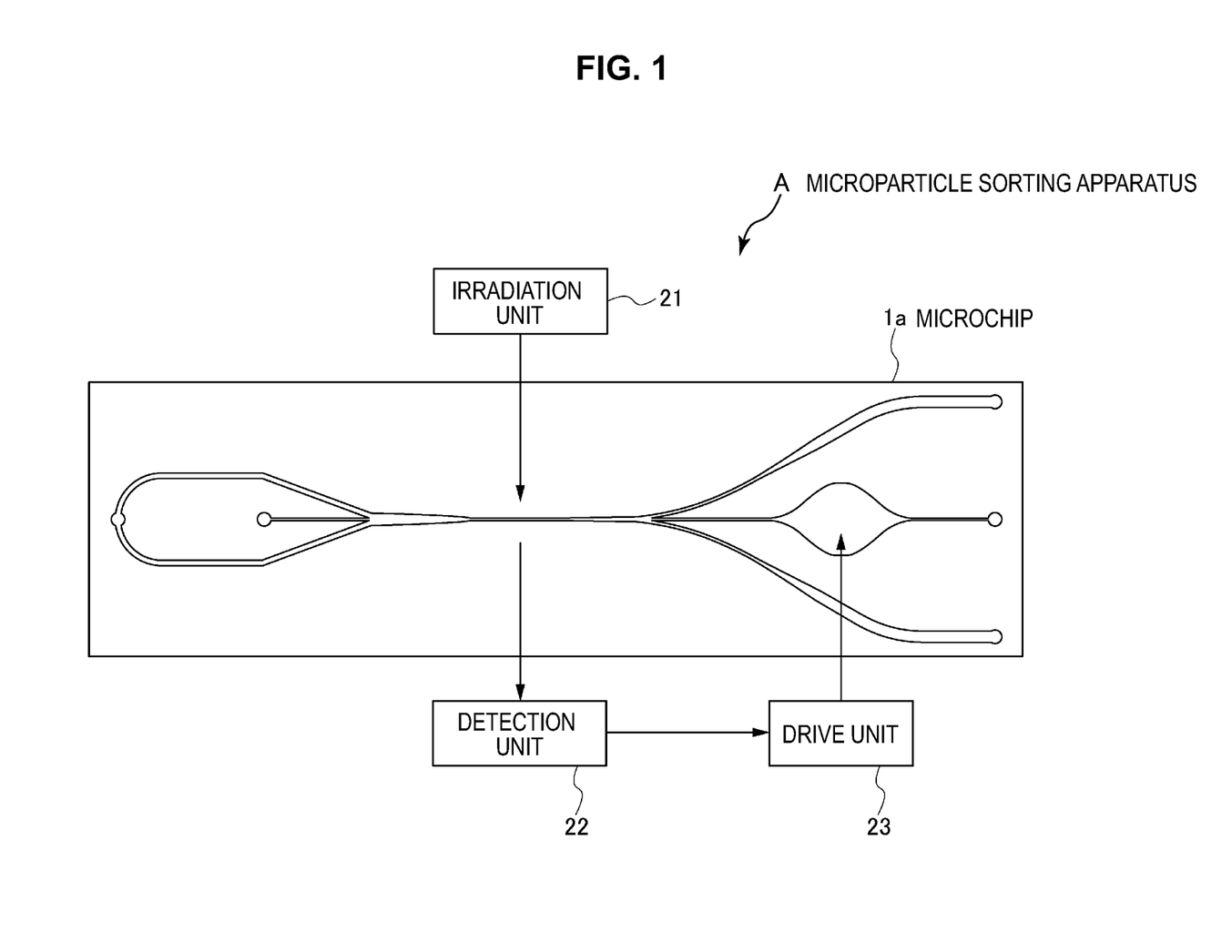
FIG. 1 is a diagram illustrating a configuration of a microparticle sorting apparatus A that is suited to implementing a microparticle sorting method according to an embodiment of the present technology.
Figure 2:
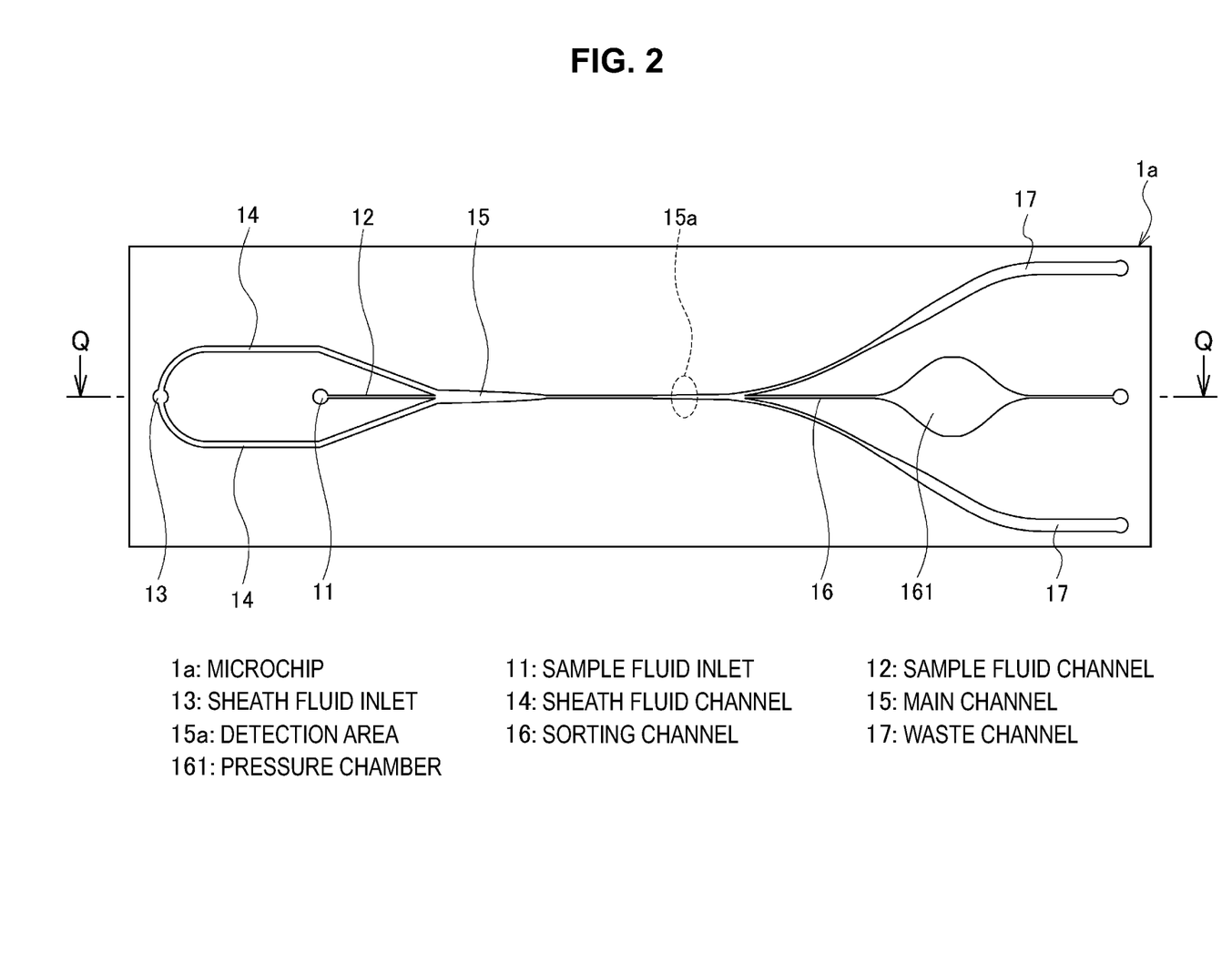
FIG. 2 is a diagram illustrating a configuration of a microchip 1a that is mounted on a microparticle sorting apparatus A.
Figure 3:
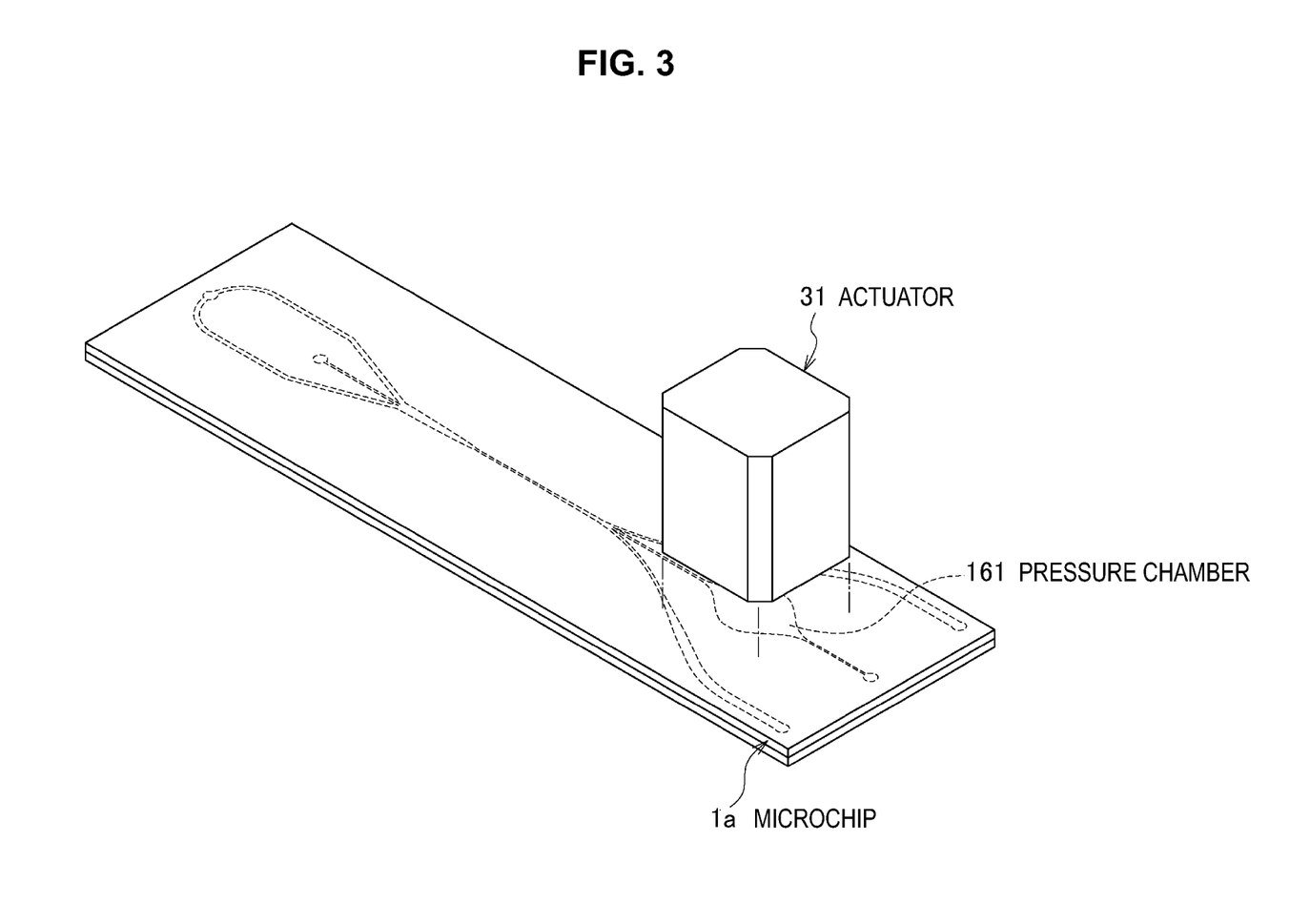
Figure 4:
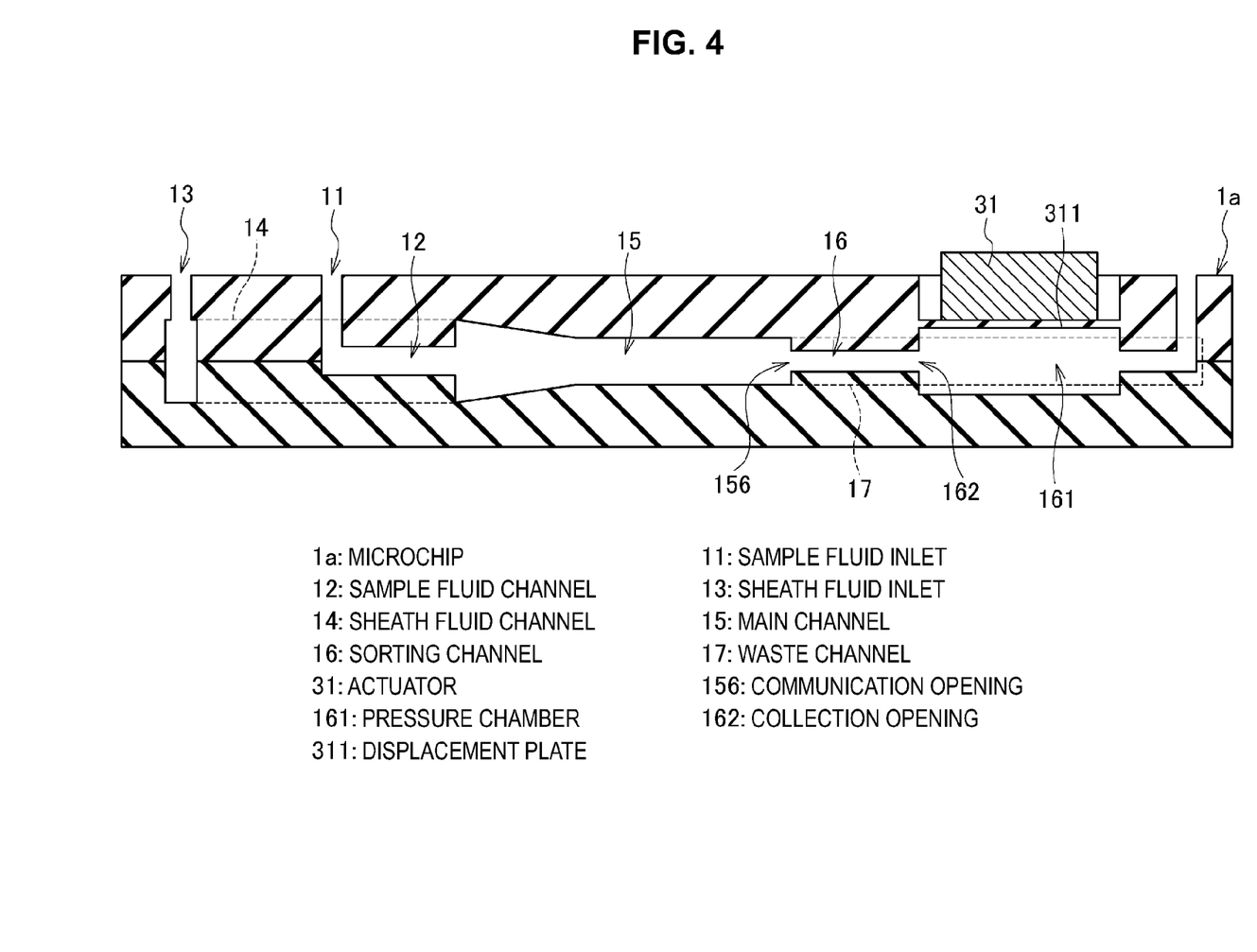

FIG. 1 is a diagram illustrating a configuration of a microparticle sorting apparatus A that is suited to implementing the microparticle sorting method according to an embodiment of the present technology. Further, FIGS. 2 to 4 are diagrams illustrating a configuration of a microchip 1a that is mounted on the microparticle sorting apparatus A. FIG. 2 is a top view, FIG. 3 is a perspective view, and FIG. 4 is a cross-sectional view along the cross-section Q-Q in FIG. 2.

The microparticle sorting apparatus A includes a microchip 1a, an irradiation unit 21, a detection unit 22, and a drive unit 23. On the microchip 1a is formed a main channel 15 through which a fluid (sample fluid) including microparticles that are the target of analysis (refer to FIG. 2). Further, an actuator 31 is arranged on the surface of the microchip 1a (refer to FIG. 3).

The irradiation unit 21 irradiates light (excitation light) on the microparticles flowing through the main channel 15 on the microchip 1a. The irradiation unit 21 includes, for example, a light source that emits excitation light and an objective lens that focuses the excitation light on the microparticles flowing through the main channel 15. The light source may be appropriately selected based on the analysis objective from among a laser diode, a SHG laser, a solid laser, a gas laser, a high luminance LED and the like. The irradiation unit 21 can optionally also have optical elements other than the light source and the objective lens.

The detection unit 22 detects fluorescence and scattered light that are emitted from the microparticles due to the irradiation with excitation light. The detection unit 22 includes an objective lens, which focuses the fluorescence and scattered light emitted from the microparticles, a detector and the like. The detection unit 22 may optionally also have optical elements other than the objective lens and the detector.

The fluorescence that is detected by the detection unit 22 may be fluorescence emitted from the microparticles themselves or fluorescence emitted from a fluorescent substance that is labeled on the microparticles. Further, the scattered light that is detected by the detection unit 22 may be various types of scattered light, such as forward scattered light, side scattered light, Rayleigh scattered light, and Mie scattering.

The fluorescence and scattered light detected by the detection unit 22 are converted into an electric signal, and the electric signal is output to the drive unit 23. The drive unit 23 determines the optical characteristics of the microparticles based on the input electric signal. Further, the drive unit 23 has a function for collecting microparticles that have been determined to satisfy a predetermined characteristic from the main channel 15 in a sorting channel 16 by applying a voltage to the actuator 31 and controlling that voltage. This function of the drive unit 23 will be described in more detail below. The drive unit 23 is configured from a hard disk in which programs and an OS for executing the below-described various processes are stored, a CPU, a memory and the like.

(Microchip Configuration)

The configuration of the microchip 1a will now be described in more detail with reference to FIGS. 2 to 4. A sample fluid that includes microparticles is introduced from a sample fluid inlet 11 into a sample fluid channel 12. Further, a sheath fluid is introduced from a sheath fluid inlet 13. The sheath fluid introduced from the sheath fluid inlet 13 is split and fed into two sheath fluid channels 14 and 14. The sample fluid channel 12 and the sheath fluid channels 14 and 14 merge to form the main channel 15. A sample fluid laminar flow fed through the sample fluid channel 12 and a sheath fluid laminar flow fed through the sheath fluid channels 14 and 14 merge in the main channel 15, and form a sheath flow in which the sample fluid laminar flow is sandwiched by the sheath fluid laminar flow.

Reference numeral 15a in the drawings denotes a detection area where excitation light is irradiated by the irradiation unit 21 and fluorescence and scattered light are detected by the detection unit 22. The microparticles are fed to the detection area 15a in a single line arranged in the sheath flow formed in the main channel 15, and are irradiated with the excitation light from the irradiation unit 21.

Figure 5:
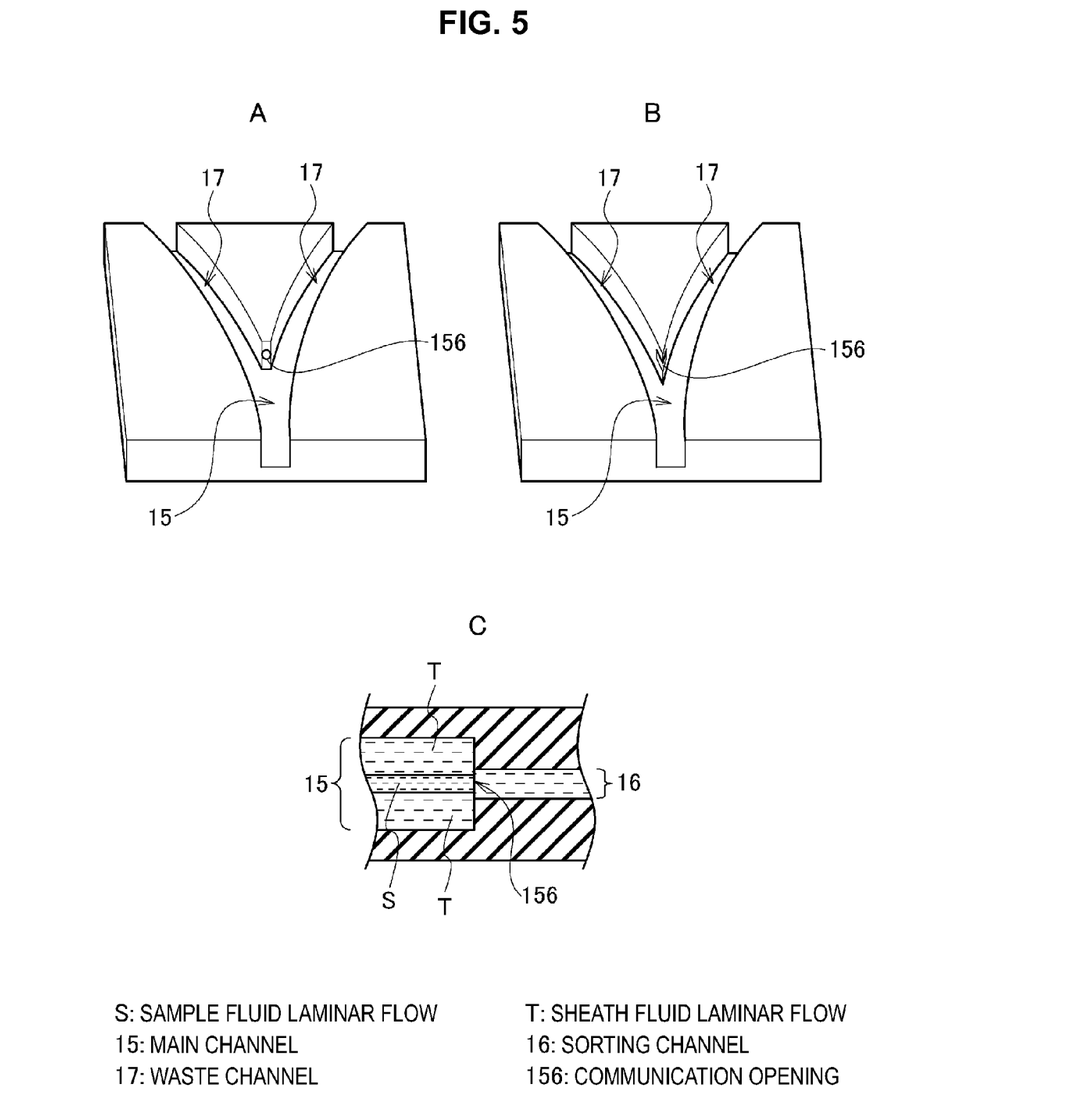

The main channel 15 splits into three channels downstream from of the detection area 15a. A configuration of the branching portion of the main channel 15 is illustrated in FIG. 5. Downstream from the detection area 15a, the main channel 15 is in communication with three branch channels, the sorting channel 16 and waste channels 17 and 17. Of these, the sorting channel 16 is a channel into which microparticles that have been determined by the drive unit 23 to satisfy a predetermined optical characteristic (hereinafter referred to as "target particles") are collected. On the other hand, microparticles that are determined by the drive unit 23 as not satisfying the predetermined optical characteristic (hereinafter referred to as "non-target particles") are not collected in the sorting channel 16, and flow into either of the two waste channels 17 and 17.

The collecting of the target particles into the sorting channel 16 is performed by generating a negative pressure in the sorting channel 16 with the actuator 31 to suck the sample fluid including the target particles and the sheath fluid into the sorting channel 16. The actuator 31 is a piezo element or similar device. The actuator 31 is arranged in contact with the surface of the microchip 1a, at a position corresponding to the sorting channel 16. More specifically, the actuator 31 is arranged at a position corresponding to a pressure chamber 161 that is provided in the sorting channel 16 as an area whose inner space has expanded (refer to FIGS. 3 and 4).

The inner space of the pressure chamber 161 is, as illustrated in FIG. 2, expanded in a planar direction (width direction of the sorting channel 16), and as illustrated in FIG. 4, expanded in a cross-sectional direction (height direction of the sorting channel 16). Namely, the sorting channel 16 is expanded in the width direction and in the height direction at the pressure chamber 161. In other words, the sorting channel 16 is formed so that its vertical cross-section increases in size in the flow direction of the sample fluid and the sheath fluid at the pressure chamber 161.

The actuator 31 causes the pressure in the sorting channel 16 to change via the surface (contact face) of the microchip 1a by producing a stretching force due to a change in the applied voltage. When a flow is produced in the sorting channel 16 due to a change in the pressure in the sorting channel 16, the volume of the sorting channel 16 simultaneously changes too. The volume of the sorting channel 16 changes until it reaches a volume that is stipulated based on the displacement of the actuator 31 corresponding to the applied voltage. More specifically, when a voltage has been applied and the sorting channel 16 is in a stretched state, the actuator 31 keeps the volume of the pressure chamber 161 small by pressing against a displacement plate 311 forming the pressure chamber 161 (refer to FIG. 4). When the applied voltage decreases, the actuator 31 generates a force in a contracting direction, whereby the pressing against the displacement plate 311 weakens and a negative pressure is generated in the pressure chamber 161.

In order to efficiently transmit the stretching force of the actuator 31 into the pressure chamber 161, as illustrated in FIG. 4, it is preferred to form a recess on the surface of the microchip 1a at the position corresponding to the pressure chamber 161, and arrange the actuator 31 in this recessed portion. Consequently, the displacement plate 311 that serves as the contact face of the actuator 31 can be made thinner, so that the displacement plate 311 can be easily displaced by changes in the pressing force generated by expansion and contraction of the actuator 31, allowing the volume of the pressure chamber 161 to change.

In FIGS. 4 and 5, reference numeral 156 denotes a communication opening of the sorting channel 16 to the main channel 15. The target particles being fed in the sheath flow formed in the main channel 15 are collected in the sorting channel 16 from the communication opening 156.

To facilitate the collection of the target particles in the sorting channel 16 from the main channel 15, as illustrated in FIG. 5C, it is desirable to form the communication opening 156 so as to open onto a position corresponding to a sample fluid laminar flow S in the sheath flow formed in the main channel 15. The shape of the communication opening 156 is not especially limited, and may be, for example, a flat opening shape like that illustrated in FIG. 5A, or a notched opening shape like that illustrated in FIG. 5B formed by cutting the channel walls of the two waste channels 17.

The microchip 1a can be configured by laminating a substrate layer on which the main channel 15 and the like are formed. The formation of the main channel 15 and the like on the substrate layer can be carried out by injection molding of a thermoplastic resin using a mold. Examples of thermoplastic resins that can be used include plastics that are known as related-art microchip materials, such as polycarbonate, polymethyl methacrylate resin (PMMA), cyclic polyolefins, polyethylene, polystyrene, polypropylene, and polydimethylsiloxane, (PDMS).

2. Microparticle Sorting Method According to an Embodiment of the Present Technology (Sorting Operation)

Next, the microparticle sorting method according to an embodiment of the present technology will be described along with operation of the microparticle sorting apparatus A.

When the user starts analysis, the microparticle sorting apparatus A drives a pump to feed the sample fluid and the sheath fluid to the sample fluid inlet 11 and the sheath fluid inlet 13 of the microchip 1a. Consequently, a sheath flow in which the sample fluid laminar flow is sandwiched by the sheath fluid laminar flow is formed in the main channel 15.

The microparticles are fed to the detection area 15a in a single line arranged in the sheath flow, and are irradiated by the excitation light from the irradiation unit 21. Fluorescence and scattered light emitted from the microparticles due to the irradiation of excitation light are detected by the detection unit 22, and converted into an electric signal. The electric signal is output to the drive unit 23.

Figure 6:
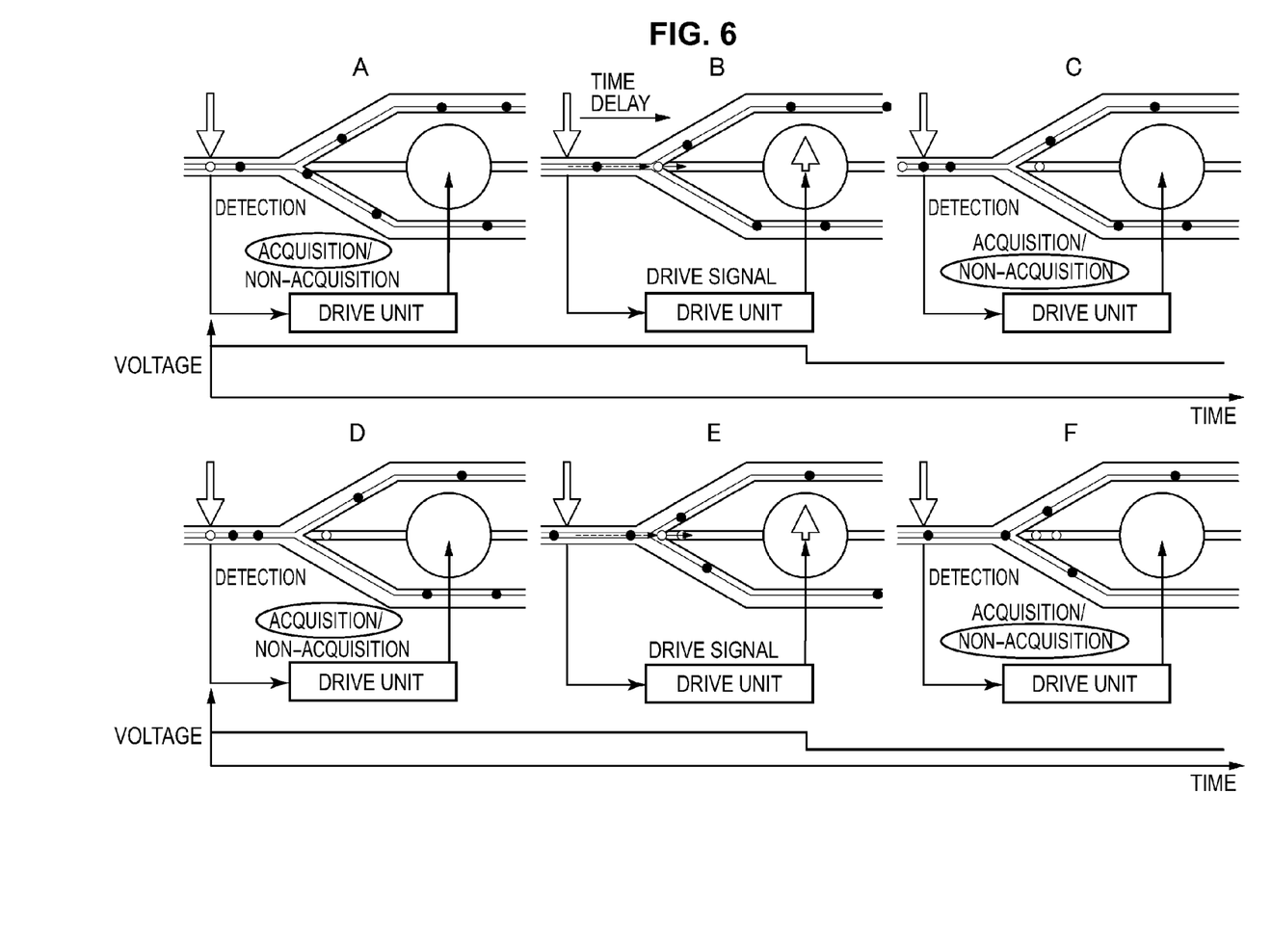
FIG. 6 is a diagram illustrating a sorting operation in the microparticle sorting apparatus A.

The drive unit 23 determines the optical characteristics of the microparticles based on the input electric signal. If a microparticle is determined to be a target particle, as illustrated in FIGS. 6A and 6B, after the time (delay period) that the target particle takes to move from the detection area 15a to the branching portion has elapsed, the drive unit 23 issues a drive signal to the actuator 31 for acquiring this microparticle. At this point, if necessary, the drive unit 23 can also be configured to drive the actuator 31 via an amplifier.

Specifically, if the actuator 31 is a piezo element, the drive unit 23 produces a negative pressure in the pressure chamber 161 by applying a voltage that causes piezo contraction, whereby the target particle is drawn from the main channel 15 into the sorting channel 16.

On the other hand, if it is determined that a microparticle is not a target particle, as illustrated in FIGS. 6C and 6D, the drive unit 23 issues a non-acquisition drive signal to the actuator 31, and performs optical characteristics determination of the next microparticle. It is noted that if the actuator 31 has received a non-acquisition drive signal, the actuator 31 does not operate.

The drive unit 23 repeats the optical characteristics determination of the microparticles and the output of a drive signal to the actuator 31 until analysis is finished (refer to FIGS. 6E and 6F), so that only the target particles accumulate in the sorting channel 16 (refer to FIG. 6F). After analysis has finished, the target particles that have been separated into the sorting channel 16 are recovered by the user. It is noted that the non-target particles that have flowed to the waste channel 17 are either accumulated in the waste channel 17, or may be externally discharged.

Figure 7:
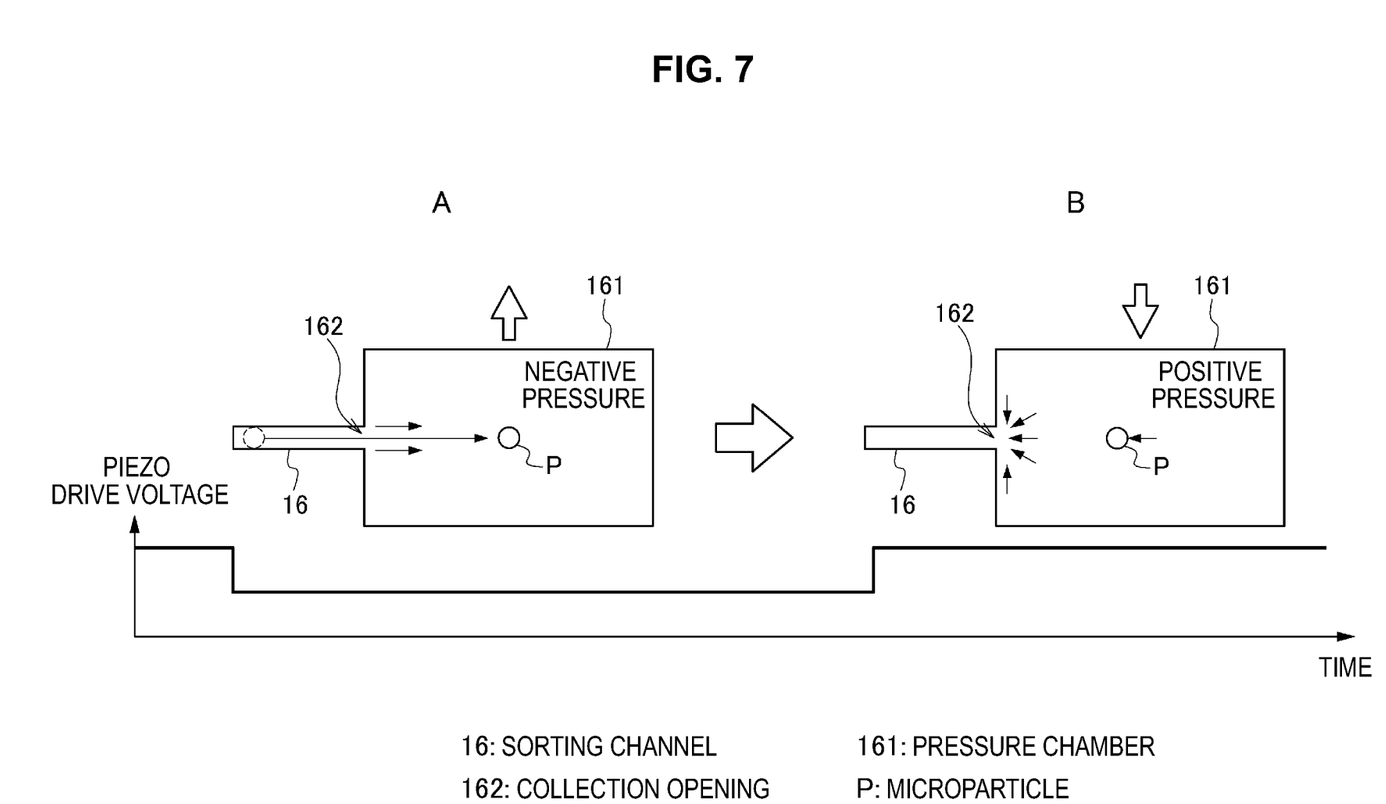

As illustrated in FIG. 7A, the target particles drawn into the sorting channel 16 are collected in the pressure chamber 161. In the drawing, reference symbol P represents a target particle that has been collected in the pressure chamber 161, and reference numeral 162 denotes a collection opening for the target particle P into the pressure chamber 161. The flow of the sample fluid including the target particle P and the sheath fluid turns into a jet when flowing into the pressure chamber 161, whose interior air has been expanded, and breaks away from the channel wall face (refer to the arrow in FIG. 7A). Consequently, the target particle P separates from the collection opening 162, and is collected at the back of the pressure chamber 161.

Since the target particles are drawn from the main channel 15 into the pressure chamber 161, the amount of expansion in the volume of the pressure chamber 161 is greater than the volume of the sorting channel 16 from the communication opening 156 until the collection opening 162 (refer to FIG. 4). Further, the amount of expansion in the volume of the pressure chamber 161 is set to be an amount that generates a negative pressure that is sufficient to cause the flow of the sample fluid including the target particle P and the sheath fluid to break away from the channel wall face at the collection opening 162. The drive unit 23 outputs to the actuator 31 a piezo contraction signal with a voltage width that corresponds to this amount of increase in volume.

Figure 8:
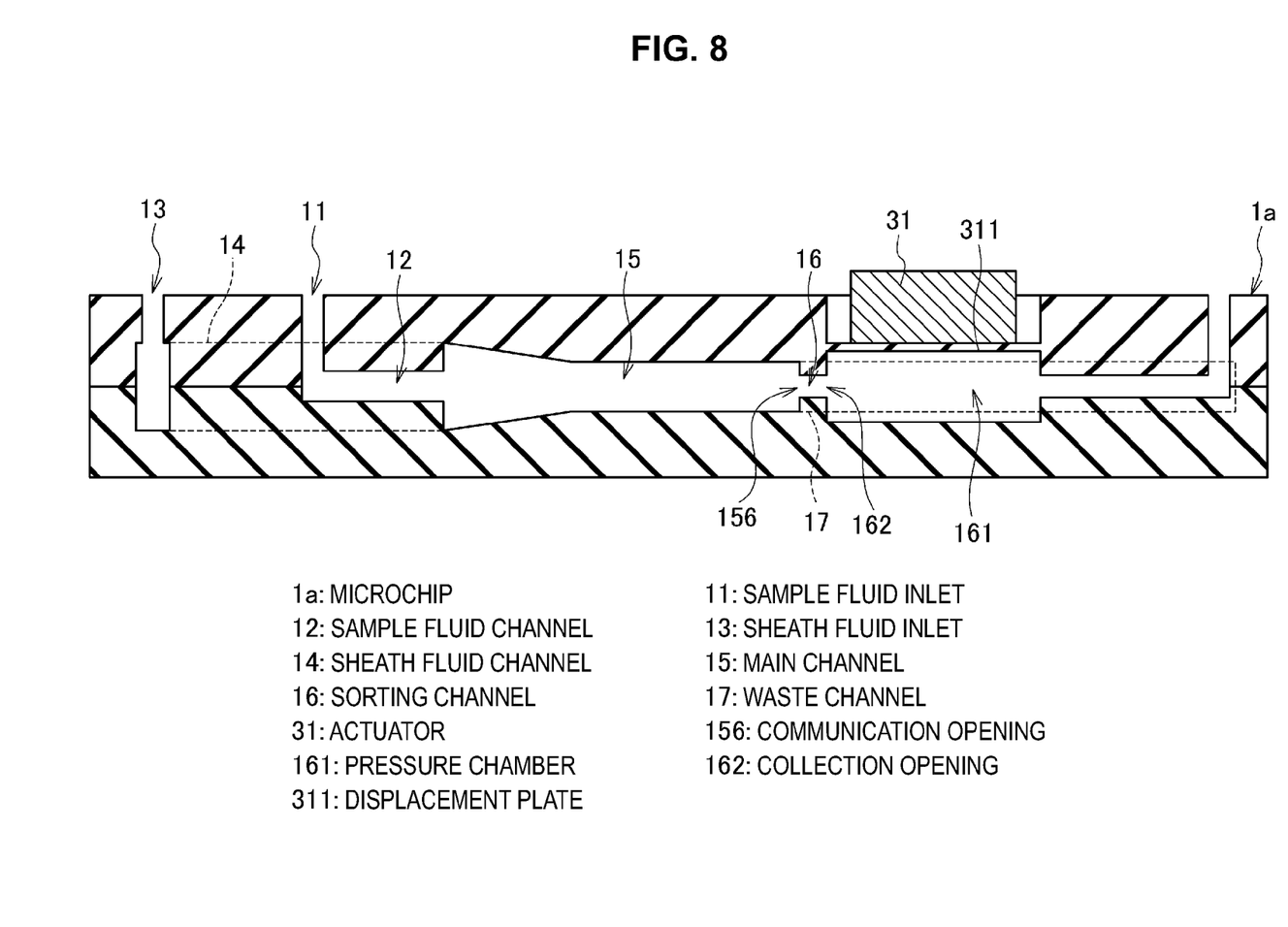

Like in the modified example illustrated in FIG. 8, the length of the sorting channel 16 from the communication opening 156 to the collection opening 162 may be designed to be shorter. The shorter the length from the communication opening 156 to the collection opening 162 is, the smaller the volume of the sorting channel 16 from the communication opening 156 to the collection opening 16 is. This means that the amount of increase in the volume of the pressure chamber 161 for drawing the target particles from the main channel 15 into the pressure chamber 161 is smaller. Consequently, the width of the voltage applied on the actuator 31 can be decreased, thereby enabling an efficient sorting operation.

Thus, by collecting the target particle P at the back of the pressure chamber 161 whose inner space has been expanded in the sorting channel 16, the target particle P can be prevented from flowing back out from the pressure chamber 161 toward the main channel 15 side even when the pressure in the sorting channel 16 reverses and becomes positive. As illustrated in FIG. 7B, even when the pressure in the sorting channel 16 is positive, since the sample fluid and the sheath fluid flow out over a wide area from the vicinity of the collection opening 162, the movement amount of the target particle P itself that has been collected at a position away from the collection opening 162 is small. Consequently, the target particle P does not flow back out, and is held in the pressure chamber 161.

(Drive Signal)

Figure 9:
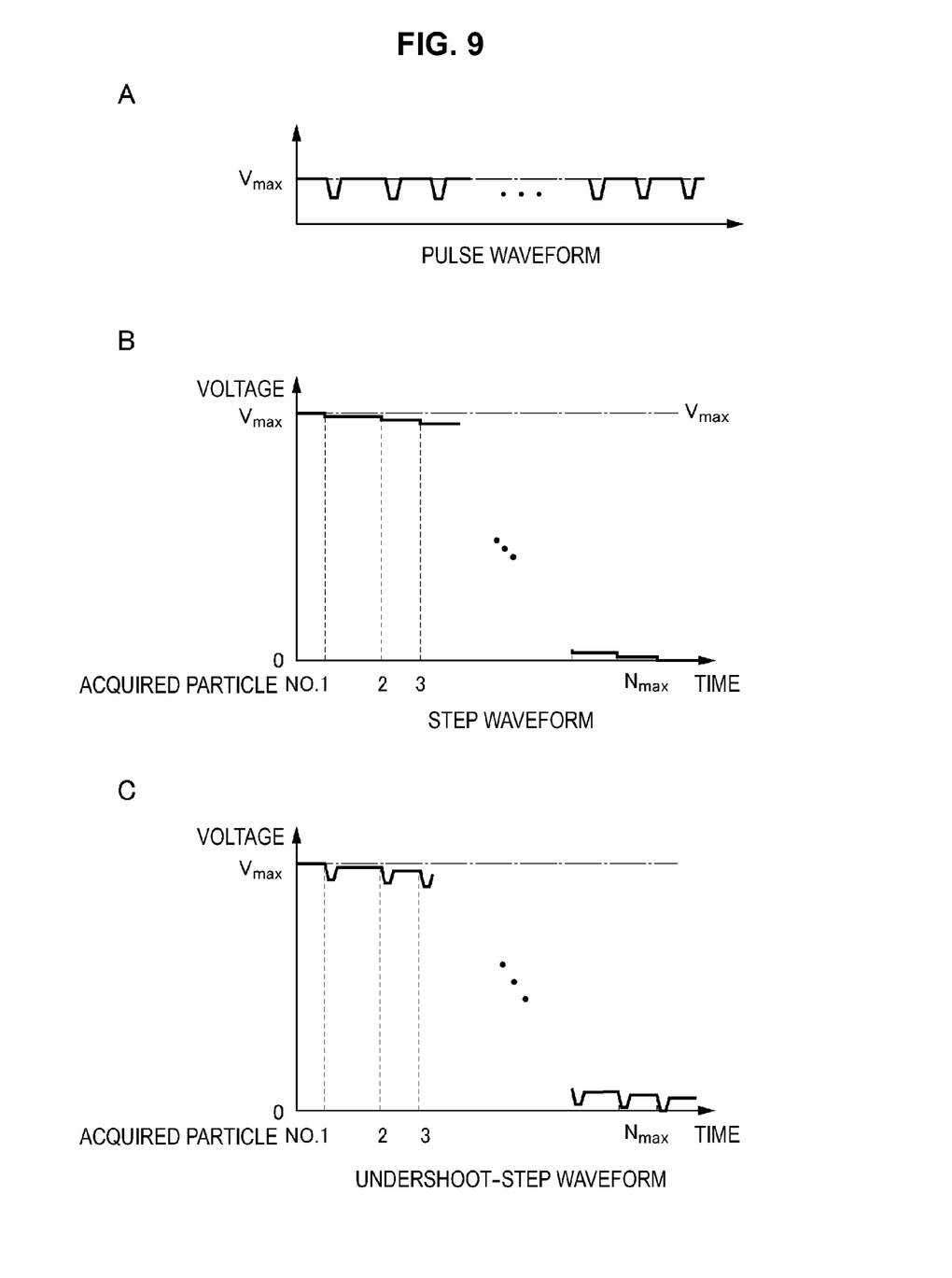
FIG. 9 is a diagram illustrating waveforms of the voltage applied on an actuator 31 from a drive unit 23.

The waveform of the voltage (drive signal when acquiring the target particles) applied on the actuator 31 from the drive unit 23 will now be described. The waveform of the voltage applied on the actuator 31 may be any of a "pulse waveform" (FIG. A), a "step waveform" (FIG. B), or an "undershoot-step waveform" (FIG. C).

Here, "undershoot-step waveform" means a waveform obtained by adding to a "step waveform" an undershoot portion in which the voltage value is lower than the step portion. The "undershoot-step waveform" can be said to be a combined wave of the "step waveform" and the "pulse waveform".

The amplitude of the pulse waveform is set so as to give a sufficient increase in volume to the pressure chamber 161 in order to draw the target particles from the main channel 15 into the sorting channel pressure chamber 161 and to make the flow of the sample fluid including the target particle P and the sheath fluid break away from the channel wall face at the collection opening 162. Further, the decrease width in the voltage value of the step waveform and the waveform portion in the undershoot-step waveform is also set so as to satisfy a similar condition.

Since the pulse waveform and the undershoot-step waveform include a waveform component that causes piezo expansion, the volume of the pressure chamber 161 increases, so that a positive pressure is generated in the sorting channel 16. Further, in the step waveform too, a positive pressure can be generated in the sorting channel 16 due to unexpected fluctuations in the voltage value. As described above, since the target particle P is collected at the back of the pressure chamber 161, the target particle P does not flow back out from the pressure chamber 161 toward the main channel 15 side even if a positive pressure is produced in the sorting channel 16.

As the waveform of the voltage applied on the actuator 31, it is preferred to employ a pulse waveform. For the step waveform and undershoot-step waveform, if the voltage applied on the actuator 31 is zero, the actuator 31 reaches the limit of its movable range, and target particles are incapable of being collected. This means that there is a limit to the maximum number of sortable microparticles. On the other hand, for the pulse waveform, there is no such limit.

Thus, according to the microparticle sorting method according to an embodiment of the present technology, by collecting the target particles in the main channel 15 in the pressure chamber 161, whose inner space has been expanded at the sorting channel 16, the target particles that have been drawn into the sorting channel 16 can be prevented from flowing back out. Consequently, separation of the target particles can be stably carried out. Further, in the microparticle sorting method according to an embodiment of the present technology, the target particles can be held even if the pressure in the sorting channel 16 is positive. Consequently, control of the drive voltage to the actuator 31 can be carried out under robust conditions. In addition, in the microparticle sorting method according to an embodiment of the present technology, the actuator 31 can be driven by a voltage with a pulse waveform. Consequently, the sorting of the target particles can be carried out without restrictions regardless of the movable range of the actuator 31.

3. Modified Example of the Microparticle Sorting Method According to an Embodiment of the Present Technology In the above-described example, a case was described in which the inner space of the pressure chamber 161 is varied by the actuator 31. Negative pressure is generated by increasing the total volume of the inner space of the sorting channel 16, and the target particles are collected and stored in the pressure chamber 161. In this example, the pressure chamber 161 has both the functions of generating the negative pressure and housing the target particles.

Figure 10:
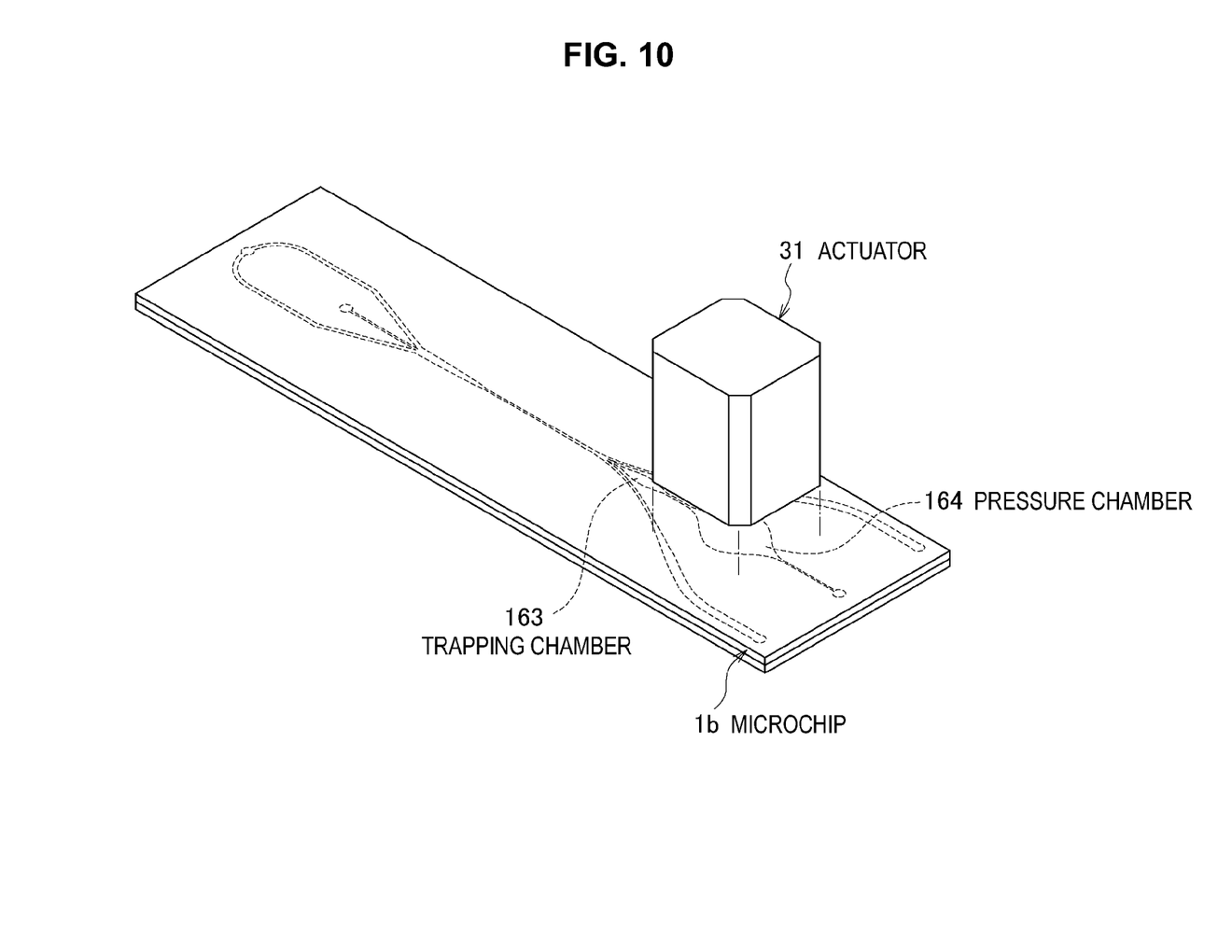
FIG. 10 is a diagram illustrating a configuration of a microchip 1b for microparticle sorting that is suited to implementing the microparticle sorting method according to an embodiment of the present technology.

FIG. 10 is a diagram illustrating a configuration of a microparticle sorting apparatus microchip when the generation of the negative pressure and the housing of the target particles are performed in separate areas in the sorting channel 16. The microchip 1b illustrated in FIG. 10 has a trapping chamber 163 and a pressure chamber 164 arranged in series in the sorting channel 16.

Similar to the pressure chamber 161 in the above-described microchip 1a, the trapping chamber 163 is configured so that the inner space is expanded in a planar direction (width direction of the sorting channel 16) and in a cross-sectional direction (height direction of the sorting channel 16). Namely, the sorting channel 16 is expanded in the width direction and in the height direction in the trapping chamber 163. In other words, the trapping chamber 163 is formed so that its vertical cross-section increases in size in the flow direction of the sample fluid and the sheath fluid, so that the target particles that are drawn into the trapping chamber 163 do not flow back out again.

In contrast, the pressure chamber 164 is formed as an area in which the inner space of the sorting channel 16 has been expanded. An actuator 31 is arranged on the surface of the microchip 1b corresponding to the pressure chamber 164. The actuator 31 causes the pressure in the pressure chamber 164 to change via the surface (contact face) of the microchip 1b. When a flow is produced in the sorting channel 16 due to a change in the pressure in the pressure chamber 164, the volume of the pressure chamber 164 simultaneously changes too. The volume of the pressure chamber 164 changes until it reaches a volume that is stipulated based on the displacement of the actuator 31 corresponding to the applied voltage. The functions of this actuator 31 are the same as those of the above-described microchip 1a.

In the microchip 1b, the target particles are collected and held in the trapping chamber 163 by a negative pressure generated due to an increase in the volume of the inner space of the pressure chamber 164. Namely, in this modified example, the pressure chamber 164 has the function of generating a negative pressure and the trapping chamber 163 has the function of housing the target particles. It is noted that, similar to the above-described microchip 1a, the waveform of the voltage applied on the actuator 31 may be any of a pulse waveform, a step waveform, or an undershoot-step waveform. Especially, by using a pulse waveform, a limit on the number of sorted target particles can be eliminated.

In the present modified example, although an example was described in which one pressure chamber as an area for generating negative pressure and one trapping chamber for housing the target particles are provided, a plurality of pressure chambers and trapping chambers, respectively, may be provided. In this case, the pressure chambers and the trapping chambers are connected in series along the sorting channel 16, and the trapping chambers are arranged so as to be positioned on the main channel 15 side with respect to the pressure chambers.

4. Microparticle Sorting Program

A microparticle sorting program for executing the above-described operations is stored in the drive unit 23 of the above-described microparticle sorting apparatus A.

The program is stored on a hard disk, read into a memory under the control of the CPU and OS, and executes the above-described sorting operation. The program can be recorded on a computer-readable recording medium. The recording medium may be any recording medium as long as it is a computer-readable recording medium. Specifically, a disk-shaped recording medium may be used, such as a flexible disk and a CM-ROM. Further, a tape type recording medium may be used, such as a magnetic tape. In addition, a configuration can also be employed in which a part of the processing may be configured from hardware, such as a DSP (digital signal processor), an ASIC (application specific integrated circuit), a PLD (programming logic device), and a FPGA (field-programmable gate array), and high-speed processing is performed in cooperation with the above-described software program.

It should be understood by those skilled in the art that various modifications, combinations, sub-combinations and alterations may occur depending on design requirements and other factors insofar as they are within the scope of the appended claims or the equivalents thereof.

Additionally, the present technology may also be configured as below.

(1) A microparticle sorting method, including:
a procedure of collecting a microparticle in a fluid that flows through a main channel in an area that is formed in a manner that a vertical cross-section increases in a flow direction of the fluid at a branch channel which is in communication with the main channel by generating a negative pressure in the branch channel.

(2) The microparticle sorting method according to (1), wherein, in the procedure, the negative pressure is generated by an actuator applying a force that deforms an inner space of the branch channel to cause a volume of the inner space to increase.

(3) The microparticle sorting method according to (2), wherein, in the procedure, an amount of increase in the volume by the actuator is greater than a volume of the branch channel from a communication opening to the area, the communication opening leading to the main channel.

(4) The microparticle sorting method according to any one of (1) to (3), wherein, in the procedure, the fluid including the microparticle flows into the area as a jet.

(5) The microparticle sorting method according to any one of (1) to (4), wherein, in the procedure, a pressure change having a pulse waveform, a step waveform, or an undershoot-step waveform is produced in the branch channel.

(6) The microparticle sorting method according to any one of (2) to (5), wherein, in the procedure, the negative pressure is generated by the actuator applying a force that deforms an inner space of the area to cause a total volume of the inner space of the branch channel to increase.

(7) The microparticle sorting method according to any one of (2) to (6), wherein the main channel and the branch channel are formed inside a microchip, and the actuator is arranged in contact with a position corresponding to the area on a surface of the microchip.

The present disclosure contains subject matter related to that disclosed in Japanese Priority Patent Application JP 2012-164038 filed in the Japan Patent Office on Jul. 24, 2012, the entire content of which is hereby incorporated by reference.

What is claimed is:

1. A microparticle sorting method, comprising:
feeding a sample fluid through a main channel to a detection area;
determining, at the detection area, whether a microparticle within the sample fluid satisfies a predetermined optical characteristic;
generating a negative pressure in a branch channel that is in communication with the main channel, wherein a vertical cross-section of the branch channel increases in a flow direction of the fluid; and
collecting the microparticle that satisfies the predetermined optical characteristic in the branch channel.

2. The microparticle sorting method according to claim 1, wherein generating the negative pressure in the branch channel includes applying, by an actuator, a force that deforms an inner space of a pressure chamber of the branch channel to cause a volume of the inner space to increase.

3. The microparticle sorting method according to claim 2, wherein, an amount of increase in the volume by the actuator is greater than a volume of the branch channel from a communication opening between the branch channel and the main channel to the pressure chamber of the branch channel.

4. The microparticle sorting method according to claim 3, wherein the sample fluid including the microparticle flows into the pressure chamber as a jet.

5. The microparticle sorting method according to claim 4, wherein a pressure change having a pulse waveform, a step waveform, or an undershoot-step waveform is produced in the branch channel.

6. The microparticle sorting method according to claim 5, wherein the negative pressure is generated by the actuator applying a force that deforms an inner space of the pressure chamber of the branch channel to cause a total volume of the inner space of the branch channel to increase.

7. The microparticle sorting method according to claim 6, wherein the main channel and the branch channel are formed inside a microchip, and the actuator is in contact with a position corresponding to the pressure chamber on a surface of the microchip.

8. A microparticle sorting apparatus comprising:
a main channel;
a branch channel including a pressure chamber, wherein the branch channel is in communication with the main channel; and
an actuator arranged at a position corresponding to the pressure chamber, wherein when a microparticle within a sample fluid fed through the main channel satisfies a predetermined optical characteristic, a negative pressure in the branch channel is generated such that the microparticle that satisfies the predetermined optical characteristic is collected in the pressure chamber of the branch channel.

9. The microparticle sorting apparatus according to claim 8, wherein the negative pressure is generated by the actuator applying a force that deforms an inner space of the pressure chamber of the branch channel to cause a volume of the inner space to increase.

10. The microparticle sorting apparatus according to claim 9, wherein an amount of increase in the volume by the actuator is greater than a volume of the branch channel from a communication opening between the branch channel and the main channel to the pressure chamber of the branch channel.

11. The microparticle sorting apparatus according to claim 10 wherein the sample fluid including the microparticle flows into the pressure chamber as a jet.

12. The microparticle sorting apparatus according to claim 11, wherein a pressure change having a pulse waveform, a step waveform, or an undershoot-step waveform is produced in the branch channel.

13. The microparticle sorting apparatus according to claim 12, wherein the negative pressure is generated by the actuator applying a force that deforms an inner space of the pressure chamber of the branch channel to cause a total volume of the inner space of the branch channel to increase.

14. The microparticle sorting apparatus according to claim 13, wherein the main channel and the branch channel are formed inside a microchip, and the actuator is in contact with a position corresponding to the pressure chamber on a surface of the microchip.

* * * * *